United States Patent [19]

Niwa et al.

[11] Patent Number: 4,788,200

[45] Date of Patent: Nov. 29, 1988

[54] METHOD AND COMPOSITION FOR TREATING ARTERIOSCLEROSIS

[75] Inventors: Ryuji Niwa, Tokorozawa; Nobuya Katagiri; Tetsuzo Kato, both of Sendai; Yoshiyasu Shitori, Tokyo; Jiro Horiuchi, Iruma, all of Japan

[73] Assignee: MECT Corporation, Tokyo, Japan

[21] Appl. No.: 89,867

[22] Filed: Aug. 27, 1987

[30] Foreign Application Priority Data

Aug. 28, 1986 [JP] Japan ................................ 61-202357

[51] Int. Cl.$^4$ .................. A61K 31/505; C07D 487/04
[52] U.S. Cl. ..................................... 514/267; 544/250
[58] Field of Search ......................... 544/250; 514/267

[56] References Cited

U.S. PATENT DOCUMENTS 4,223,031  9/1980  Covington et al. ................. 514/267
4,232,024 11/1980  Winter et al. ....................... 514/267
4,471,117  9/1984  Sipido ................................. 544/250

FOREIGN PATENT DOCUMENTS 0063680  4/1986  Japan .................................. 514/267

OTHER PUBLICATIONS

Niwa et al., Chem. Pharm. Bull., vol. 32(10), pp. 4149–4153 (1984).
Niwa et al., Chemical Abstracts, vol. 102:166686c (1985), Abstract of Niwa, et al(R).

*Primary Examiner*—Donald G. Daus
*Assistant Examiner*—Diana G. Rivers
*Attorney, Agent, or Firm*—Jacobs & Jacobs

[57] ABSTRACT

A medicament for curing arteriosclerosis which comprises pyrimido [2,1-b] benzothiazole derivative.

10 Claims, No Drawings

METHOD AND COMPOSITION FOR TREATING ARTERIOSCLEROSIS

BACKGROUND OF THE INVENTION

1. Field of the Invention

The present invention relates to a medicament for treating arteriosclerosis which comprises pyrimido[2,1-b]-benzothiazole derivative.

Medical treatment for arteriosclerosis aim to prevent the progress of arteriosclerosis and/or to prevent the occurrence thereof. A further object of such a medical treatment is to prevent occurrence of arteriosclerosis when symptoms of the disease have already been recognized.

In order to preclude occurrence of arteriosclerosis, it is necessary to remove the factors which induce the disease, such as hyperlipidemia, smoking or corpulence. On the other hand, it has been pointed out that blood platelets have a close relation to the occurrence of arteriosclerosis, and according to one hypothesis thrombopoiesis is the main cause of arteriosclerosis. Under such circumstances, anticoagulants for inhibiting coagulation of blood platelets have been used as medicaments for prevention of arteriosclerosis.

In one of its aspects, this invention relates to a medicament for alleviating the hyperlipidemia which is considered as the principal factor inducing arteriosclerosis. More particularly, the present invention relates to a medicament containing a pyrimidobenzothiazole derivative as an efficacious ingredient for hyperlipidemia.

According to another aspect, this invention relates to an anticoagulant for inhibiting coagulation of blood platelets, which contains a pyrimidobenzothiazole derivative, as an efficacious ingredient, for controlling blood platelet prostaglandin synthesis thereby to alleviate the symptoms of thrombosed or blocked arteria disease.

2. Description of the Related Art

Heart disease caused by troubles in the coronary arteries are the leading cause of death in the United States of America, and almost all of the patients suffering such diseases are afflicted with arteriosclerosis.

It has been considered such diseases or symptoms have a close relation with improper diet, corpulence, high serum cholesterol level, lack of physical activity, mental stress, hypertension and smoking.

Likewise in Japan, it is anticipated that patients afflicted by such diseases will increase in the future due to similar causes, particularly due to the tendency of modern Japanese to eat high calorie meals similar to the peoples of Europe and America. It may therefore be said that such arteriosclerotic diseases are modern diseases in advanced nations.

Meanwhile, patients who are troubled with hyperlipidemia are seriously affected by increase in lipoproteins, particularly the increase in low density lipoprotein (LDL) or beta-very low density lipoprotein ($\beta$-VLDL).

For the symptoms caused by hyperlipidemia, it is known that the precipitation of lipid (esters of long-chain fatty acids and alcohols and analogues thereof) depends upon the lipid content of blood serum and that gruel-like spots are formed by the sedimentation of lipid. Formation and spreading of gruel-like spots can be suppressed or reduced by the use of a drug composition or medicament for eliminating the hyperlipidemia.

The drug compositions which are presently used in clinical applications for eliminating hyperlipidemia have the functions or effects which may be roughly divided into the following groups:

(1) Inhibiting synthesis of cholesterol in liver;
(2) Accelerating catabolism (dissimilation) and discharge of cholesterol;
(3) Suppressing absorption of cholesterol through the intestinal tract; and
(4) Activation of lipase activity of lipoprotein.

Examples of the drug ingredients which have the functions or effects as classified hereinabove will be set forth below.

(1) Clofibrate[ethyl-2-(p-chlorophenoxy)-2-methylpropionate] and simfibrate;
(2) Thyroxine and Pantetheine;
(3) Cholestyramine and Melinamide; and
(4) Dextran sulfate.

However, it has not yet been found that pyrimido[2,1-b]benzothiazole derivatives have the effect of curing hyperlipidemia.

After studies on the pyrimido[2,1-b]-benzothiazole derivatives, we have found that the compounds of this invention have the effect of decreasing LDL and $\beta$-VLDL which tend to cause an injury of endothelium and arteriosclerosis. The compounds of this invention have a further effect of inhibiting coagulation of blood platelets, thus preventing blockage of blood flow and suppressing coagulation of blood.

The conventional drugs, which have been called "blood platelet coagulation inhibitors" are used mainly for prevention of formation of thrombus since a once-formed thrombus is hard to re-dissolve or removed from the blood.

On the other hand, it has recently been pointed out that thrombosed diseases, such as ischemic disorder, disorder in cerebral blood vessel and diabetes millitus, are very serious. It is well known that the formation of thrombus is affected by the blood vessel wall, the composition of the blood and the condition of blood flow, and it is further regarded as important to consider the role played by the endothelium of the blood vessels, activation of blood platelets, formation of fibrin, failure of fibrin dissolution system, change in blood flow and reticuloendothelial system. Particularly important factors are adherence of blood platelets on the impaired blood vessel wall, releasing of the contents in blood platelets and coagulation reaction thereof.

Studies on and elucidation of the function of prostaglandin (PG) and derivatives thereof have been pursued. For example, prostaglandin (PG) and derivatives thereof have been synthesized from the components constituting the blood platelet membrane when the blood platelets are stimulated. Specifically, when blood platelets are activated, arachidonic acid is freed from phospholipid of the blood platelet membrane under the action of phospholipase and then acted on by cyclooxygenase to produce $PGG_2$ and $PGH_2$ which are PG endoperoxides. Thereafter, these PG endoperoxides react with Thromboxane $A_2$ synthesis enzyme to product Thromboxane $A_3$ ($TXA_2$). The $TXA_2$ has an extremely high blood platelet coagulation function. On the other hand, the blood vessel wall contains an enzyme which converts $PGG_2$ and $PGH_2$ to prostacycline ($PGI_2$). The $PGI_2$ has a function of inhibiting coagulation of blood platelets of a strength competine with the function of $TXA_2$. In view of the above, it has been considered that the balance between the $TXA_2$ and the PGI$_2$ is important in connection with the formation of thrombus.

In the case of not only the thrombosed diseases but the blocked arteria diseases, it is known that the TXB$_2$ (stabilizing product of metabolism of TXA$_2$) value of the patient assumes a significantly high value as compared to that of a healthy person. This suggests that the blood platelets of such a patient are in a condition of easy coagulating, and in view of this tendency, a variety of blood platelet coagulation inhibitors are increasingly used for the prevention or remedy of these diseases in recent clinical treatments.

Furthermore, inhibition of metastasis of cancer by the use of an anti-Thrombus agent or drug has been tried recently.

Meanwhile, the blood platelet coagulation inhibitors presently used in clinical applications may be divided into following two groups in consideration of their functions or effects.

The first group includes those which are "inhibitors for synthesis of prostaglandin in blood platelets"; and the second groups includes those which are "inhibitors for c-AMP phosphodiesterase" or "accelerators for adenylate cyclase."

Known inhibitors for synthesis of prostaglandine in blood platelets, are Aspirin, indomethacine and imidazole derivatives.

As the "inhibitors for c-AMP phosphodiesterase" or "accelerators for adenylate cyclase", papaverine and dipyridamol have been known for the former and ticlopidine has already been known and used widely for the latter.

It has been further recognized recently that Aspirin, dipyridamol and ticlopidine have the effect of inhibiting metastasis of cancer as shown by the results of experiments using animals.

However, an excellent blood platelet coagulation inhibitor has not yet been found from the group of pyrimido[2,1-b]benzothiazole derivatives.

According to one of its aspects, this invention has as its object to provide a pyrimido[2,1-b]benzothiazole derivative which has improved function of inhibiting coagulation of blood platelets that is superior to various known blood coagulation inhibitors.

DESCRIPTION OF THE INVENTION

The present invention is based on the finding that some pyrimido[2,1-b]benzothiazole derivatives have the surprising function of reducing fat content in blood, to a degree beyond expectation, when the activities thereof are examined using mice as the test animals in experiments.

The present invention is also based on a further finding that some pyrimido[2,1-b]benzothiazole derivatives have the surprising function of inhibiting coagulation of blood platelets, to a degree beyond expectation, when the activities thereof are examined using rabbits as the test animals in experiments.

Briefly stated, the present invention provides a medicament for curing arteriosclerosis, particularly an agent for alleviating high fat content in blood or an anticoagulant for inhibiting coagulation of blood platelets, which comprises a pyrimido[2,1-b]benzothiazole derivative represented by the following formula (I):

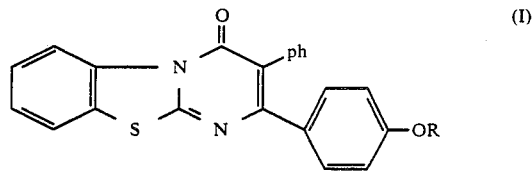

wherein ph is a substituted or unsubstituted phenyl group, R is an alkyl group having 1 to 5 carbon atoms.

The compounds used in this invention and represented by the formula (I) may be, for example, prepared as follows:

(A preparation process will be described in detail by referring to specific examples.)

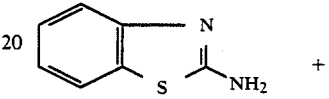

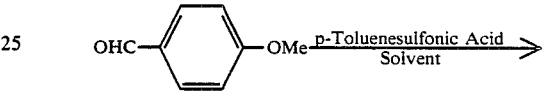

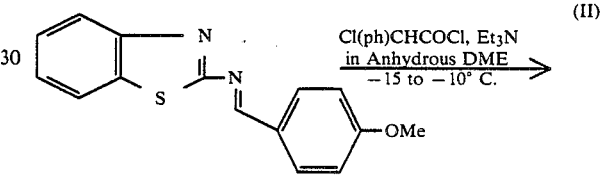

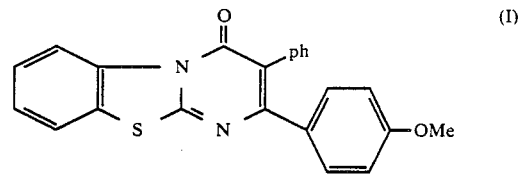

EXAMPLE 1

(A) Preparation of 2-(p-Anisylideneamino)benzothiazole Compound (II)

2-Aminobenzothiazole (10.5 g, 0.07 mol) and p-anisaldehyde (9.53 g, 0.07 mol) were heated and refluxed with p-toluenesulfonic acid (0.05 g) in a solvent (xylene: 60 ml) contained in a Dien-Stark vessel while removing water. A crystal obtained by distilling off the solvent under reduced pressure was recrystallized in acetone to prepare 10.3 g (Yield: 55%) of a compound (II) in the form of yellow needle-like crystal and having a melting point of 89° to 91° C. (lit, Melting Point: 91° to 92° C., M. Sakamoto et al., Chem. Pharm. Bull., 24, 2532 (1976)).

Characteristic Features of the Compound (II):
IR (KBr): 1600 cm$^{-1}$.
$^1$H-NMR (CD$_3$OD—CDCL$_3$) δ: 3.83 (3H, s, OMe), 6.83–8.10 (8H, m, ring-H), 9.00 (1H, s, CH=N).

Preparation of 2-(p-methoxyphenyl)-3-phenylpyrimido[2,1-b]benzothiazole-4(4H)-one Compound (I):

A solution of 2-(p-anisylideneamino)benzothiazole (2.68 g, 0.01 mol) and triethylamine (1.52 g, 0.015 mol)

in anhydrous 1,2-dimethoxyethane (DME, 120 ml) was dropwisely added with a solution of α-chlorophenylacetyl chloride (2.27 g, 0.012 mol) in anhydrous DME (10 ml) while agitating and cooling by a salt-ice bath (−15° to −10° C.). After the completion of dropwise addition, the temperature of the reaction solution was returned to room temperature, followed by agitation for 2 hours, and then DME was distilled off under reduced pressure. Chloroform (150 ml) was added to the residue, and the chloroform phase was rinsed with water (100 ml×3 times). After drying with sodium sulfate anhydride, the solvent was distilled off under reduced pressure. The crystalline residue obtained was recrystallized from acetone to prepare 2.64 g (Yield: 69%) of a compound (I) of colorless needle-like crystal form having a melting point of 233° to 234° C.

Characteristic Features of Compound (I):

Result of Ultimate Analysis: $C_{23}H_{16}N_2O_2S$ Calc.: C, 71.85: H, 4.20; N, 7.29. Found: C, 71.80; H, 4.29; N, 7.10.

IR(KBr): 1665, 1600 cm$^{-1}$.

$^1$H-NMR (CF$_3$CO$_2$H—CDCL$_3$) δ: 3.90 (3H, s, OMe), 6.82–8.03 (12H, m, ring-H), 9.10 (1H, m, 6-H).

MS m/e: 384 (M+).

METHOD OR ROUTE FOR ADMINISTRATION OF THE COMPOUNDS OF THE INVENTION

The pyrimido[2,1-b]benzothiazole, according to this invention, may be administered either orally or through other routes.

Accordingly, the medicament for curing arteriosclerosis according to this invention may be formulated in various "oral administration" forms, such as powder form, tablets, capsules, granules and liquid form; or in a variety of "non-oral administration" forms, such as hypodermic, intramuscular or intraveous injection, in the form of a mixture with a carrier liquid, paste, tincture, plaster or suppository.

The aforementioned formulations may be prepared through various processes which have been known per se. For example, powders, tablets, capsules or granules may be prepared by combining any of the pyrimido[2,1-b]benzothiazole derivatives (I) with suitable additives including excipiens such as starch, lactose or mannitol; binders such as sodium carboxymethyl cellulose or hydroxypropyl cellulose; disintegrators such as crystalline cellulose or potassium carboxymethyl cellulose; lubricants such as talc or magnesium stearate; and fluidity improvers such as soft silicic acid anhydride.

The compound (I) may also be in the form of a hypodermic, intramuscular or intravenous injection while preparing an aqueous solution used for injection or preparing a powder which is dissolved to form an injection solution when in use, in accordance with the conventional methods.

In preparation of a suppository, the compound (I) is dispersed in a commonly used base, such as cacao fats or synthetic oils and fats, by a conventional method, followed by solidification of the dispersion.

The dosage amount of the thus prepared drug composition for the medical treatment of arteriosclerosis, according to this invention, may be varied depending on the degree of disease and the weight of the patient; and preferably ranges from 0.05 to 5.0 g a day when it is used for hyperlipidemia, and preferably ranges from 0.4 to 1.8 g a day when it is used as an anticoagulant for inhibiting coagulation of blood platelets.

The acute toxicity of the compound (I) of the invention was tested. The result will be set forth below.

TEST ON ACUTE TOXICITY

The compound (I) was administered to mice in an amount of 300 mg/kg orally or abdominally. No changes were observed for either the cases of oral or 200 mg/kg abdominal administration. Also, no substantial change was observed when it was administered 5 times successively in a dosage amount of 100 mg/kg per time.

The present invention will now be described more specifically by referring to further Examples thereof. However, it is to be noted here that the following Examples should be construed by way of example only and the invention is not limited thereto. For example, the compounds of this invention may be formulated in other than the following formulations, in combination with various buffers, antiseptics, isotonics, stabilizers, viscosity increasing agents and other bases (these agents being generally referred to as "carriers").

EXAMPLE 2

Effect against Hyperlipidemia Obtainable by the Addition of Compound (I) (Demonstration 1)

Six mice were bred with high cholesterol-cholic acid feeds for 7 days so as to induce hyperlipidemia; one half of the total dose of each compound (I) as set forth in Table 1 was orally administered at the sixth day and the other half was orally administered at the seventh day. After starving the mice for one night, the cholesterol content of the blood serum of the respective mice was determined. It was judged that the tested compound had the desired activity (of reducing fat content of blood) when the cholesterol content of the blood serum was decreased by 15% or more as compared to that of the mice of the control group.

TABLE 1

| Administered Agent | Method of Administration | Dose | Reduction Rate of Cholesterol in Blood Serum (%) |
|---|---|---|---|
| Compound (I) | Oral | 25 mg/kg | 16 |
| Compound (I) | Oral | 10 mg/kg | 11 |
| D-thyroxine | Oral | 10 mg/kg | 30 |

As can be seen from the results of Table 1, the compound (I) of this invention showed a pharmaceutical efficacy amounting to about 2/5 of that of the control agent, i.e. D-thyroxine.

EXAMPLE 3

Effect against Hyperlipidemia Obtainable by the Addition of Compound (I) (Demonstration 2)

Similar experiments were conducted as in Example 2, and it was judged that the tested compound had the desired activity (of reducing fat content in blood) when the content of lipoproteins precipitated by heparin (corresponding to the fractions of LDL and VLDL) in the blood serum of the tested group was decreased by 20% or more as compared to that of the mice of control group. Decrease of atheromic β-LDL or increase of HDL could be estimated when the ratio of lipoproteins precipitated by heparin to cholesterol (HPL/cholesterol) was not more than 0.92.

TABLE 2

| Administered Agent | Method of Administration | Dose | Decrease of HPL (%) | HPL Cholesterol |
|---|---|---|---|---|
| Compound (I) | Oral | 25 mg/kg | 23 | 0.92 |
| Compound (I) | Oral | 10 mg/kg | 17 | — |
| D-Thiroxicine | Oral | 10 mg/kg | 35 | 0.93 |

As can be seen from the results in Table 2, the compound (I) of this invention showed a pharmaceutical efficacy amounting to about 2/5 of that of the control agent D-thiroxicine.

EXAMPLE 4

Anticoagulating Function for Inhibiting Coagulation of Blood Platelets

White Japanese native species male rabbits each having a body weight of from 2.5 to 4.0 kg were used. The state of health of the rabbits was checked by visual examination for such as diarrhea and scabies in the ears, and the number of blood platelets and the hematocrit value of the individual rabbits were determined using the blood taken from the auricular vein of the individual rabbits. Rabbits each having a number of blood platelets of from $30 \times 10^4$ to $50 \times 10^4/m^3$ and a hematocrit value of from 30 to 40% were selected and the thus selected rabbits were fed for a pre-breeding period of one week, and then the number of blood platelets and the hematocrit value of the thus bred rabbits were determined again. Those that had a number of blood platelets and a hematocrit value within the ranges as aforementioned were subjected to the following test.

Using an injection tube treated with silicone, blood was taken from the auricular artery so that the ratio of blood to a 3.8% sodium citrate solution was 9 to 1 by volume, and the content of the tube was subjected to centrifugal separation at 100 to 140 g for 10 minutes. The supernatant was separated as platelet rich plasma (PRP), and the lower phase was further subjected to centrifugal separation at 450 g or 300 g for 10 minutes to obtain a platelet poor plasma (PPP). After subjecting the PRP to centrifugal separation at 800 g for 10 minutes, precipitated blood platelets were rinsed one time with a 5 m MEDTA deprived of $Ca^{2+}$ and $MG^{2+}$ and Hepes-Tyrode buffer (pH 7.4), and then suspended in Hepes-Tyrode buffer (pH 7.4) to obtain rinsed blood platelets. In the coagulation experiment, the number of blood platelets in PRP was directly counted by the Brecher-Cronkite method to control the same within the range of from $50 \times 10^4$ to $70 \times 10^4/mm^3$.

Using an aggregometer, PRP was added with each of specimen drugs, followed by incubation at 37° C. for a predetermined time period (2 minutes), and an aggregation provoker (arachidonic acid, 50 mcg/ml) was added and then subjected to measurement.

The control drug used was Aspirin. The results are shown in Table 3.

As can be clearly seen from Table 3, the compound (I) of the invention showed an efficacy 2.5 times as high as that of the control drug, Aspirin.

TABLE 3

| Added Drug | Dosage Method | Dose | Response |
|---|---|---|---|
| Compound (I) | in vitro | 1 γ | 100 |
| Compound (I) | in vitro | 0.5 γ | 0 |
| Aspirin | in vitro | 2.5 γ | 100 |

Note: γ = μg/ml

EXAMPLE 5

Preparation of Enteric Film Coated Tablet 100.0 g of the compound (I), 79.0 g of corn starch, 90.0 g of lactose and 4.0 g of crystalline cellulose were intimately mixed in a mixer, and then added with 8.0 g of hydroxypropyl cellulose dissolved in ethanol, followed by thorough kneading. The admixture was granulated, using a screen having 0.5 mm meshes, by an extrusion granulator. The thus formed granules were dried using a conventional process, the dried granules were added and mixed with 2.0 g of talc and 1.0 g of magnesium stearate, and tablets were formed using a conventional tablet forming machine. Tablets each having a weight of about 284 mg and a diameter of about 12 mm were produced.

Separately, a coating solution was prepared by dissolving 110.0 g of methacrylic acid/methyl methacrylate, 10 g of polyethylene glycol-6000 and 30 g of talc in 500 ml of ethanol. The tablets were coated with the coating solution by a conventional spraying process. Film coated tablets each having a weight of about 300 mg were thus produced.

Each of the tablets was tested in accordance with the disintegration test method for testing enteric-coated preparations stipulated in The Pharmacopoeia of Japan (hereinafter referred to as "PJ"). The result was that the tablet was not disintegrated in the first solution (an artificial gastric juice, pH 1.2) even after shaking for an hour and that it was distintegrated within a period of about 8 to 10 minutes in the second solution (an artificial intestinal juice, pH 6.8). Each of the enteric film coated tablets of this Example contained 100 mg of the compound (I).

EXAMPLE 6

Preparation of Enteric-coated Granules

Using a mixer, 100.0 g of the compound (I), 294.0 g of corn starch and 490.0 g of lactose were thoroughly mixed together, and then added with 1.5 g of hydroxypropyl cellulose dissolved in ethanol, followed by thorough kneading. Granules were formed from the admixture, dried and then screened by a conventional process.

Separately, a coating solution was prepared by dissolving 110.0 g of methacrylic acid/methyl methacrylate, 10 g of polyethylene glycol-6000 and 30 g of talc in 500 ml of ethanol. 800 g of the granules, prepared as aforementioned, were put into a flow coater where they were coated with the coating solution by spraying, whereby about 1,000 g of enteric-coated granules were produced.

The result of a disintegration test conducted using a disintegrator stipulated in PJ revealed that the granules were not disintegrated even after being shaken in an artificial gastric juice having a pH value of 1.2, and disintegrated within 6 to 8 minutes when they were immersed in an artificial intestinal juice having a pH value of 6.8.

Each of the granules produced in this Example contained 100 mg of the compound (I) per 1 g of the prepared formulation.

EXAMPLE 7

Preparation of Enteric Capsules

Using a mixer, 100.0 g of the compound (I), 37.0 g of corn starch and 80.0 g of lactose were thoroughly mixed together, and then added with 3.0 g of hydroxypropyl cellulose dissolved in ethanol, followed by thorough kneading. The subsequent procedures were similar to those as employed for the preparation of the enteric-coated granules. About 220 g of the granules were coated with the same coating solution as used for the preparation of the enteric-coated granules of the preceding Example to obtain about 240 g of coated granules. About 240 mg of the coated granules were charged in each capsule, by a conventional process, to obtain enteric capsule-form preparation.

The result of a disintegration test conducted using a disintegrator stipulated in PJ revealed that the capsules were not disintegrated even after being shaken in an artificial gastric juice having a pH value of 1.2, and disintegrated within 8 to 10 minutes when they were immersed in an artificial intestinal juice having a pH value of 6.8.

Each of the capsules produced in this Example contained 100 mg of the compound (I).

What is claimed is:

1. A composition for the treatment of arteriosclerosis or hyperlipedemia, or for inhibiting coagulation of blood platelets, comprising an effective amount of a pyrimido [2,1-b]benzothiazole of the formula (I):

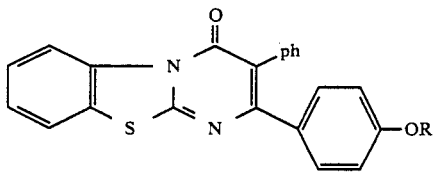

wherein ph is a phenyl group, and R is an alkyl group having 1 to 5 carbon atoms, in combination with a pharmaceutically acceptable carrier.

2. The composition according to claim 1, in an orally administered form.

3. The composition according to claim 1, wherein said carrier comprises a stabilizer, preservative, buffer or isotonizer.

4. A method for the treatment of an animal suffering from arteriosclerosis, which comprises administering to the sufferer an effective amount of a pyrimido [2,1-b]benzothiazole of the formula (I):

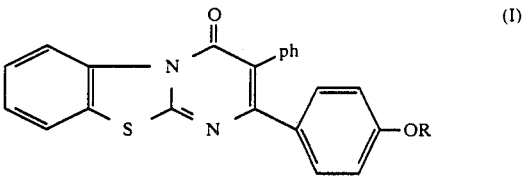

wherein ph is a phenyl group, and R is an alkyl group having 1 to 5 carbon atoms.

5. The method according to claim 4, wherein said compound is orally administered.

6. A method for treating an animal suffering from hyperlipedemia, which comprises administering to the sufferer an effective amount of a pyrimido [2,1-b]benzothiazole of the formula (I):

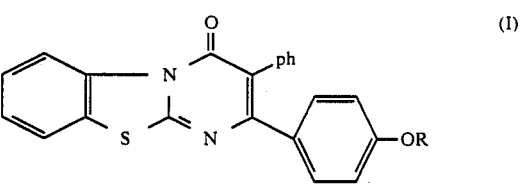

wherein ph is a phenyl group, and R is an alkyl group having 1 to 5 carbon atoms.

7. The method according to claim 6, wherein said compound is orally administered.

8. A method for inhibiting coagulation of blood platelets in an animal, which comprises administering to the animal in need thereof an effective amount of a pyrimido [2,1-b]benzothiazole of the formula (I):

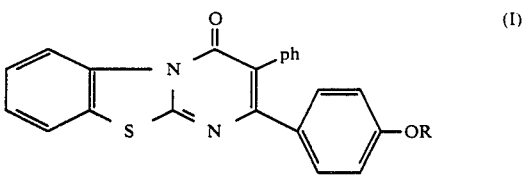

wherein ph is a phenyl group, and R is an alkyl group having 1 to 5 carbon atoms.

9. The method according to claim 8, wherein said compound is orally administered.

10. The method according to claim 8, wherein said compound is administered other than orally.

* * * * *